United States Patent [19]

Swenson, Jr.

[11] 4,109,515

[45] Aug. 29, 1978

[54] PHOTOELASTIC STAMPING ANALYSIS

[75] Inventor: Willard E. Swenson, Jr., Troy, Mich.

[73] Assignee: Chrysler Corporation, Highland Park, Mich.

[21] Appl. No.: 684,526

[22] Filed: May 10, 1976

[51] Int. Cl.$^2$ .................. G01N 3/28; G01B 11/18
[52] U.S. Cl. ........................................ 73/88 A; 356/34
[58] Field of Search ............... 73/88 A; 356/32, 34, 356/35, 36

[56] References Cited

U.S. PATENT DOCUMENTS

| 3,034,395 | 5/1962 | Zandman | 356/34 |
| 3,847,481 | 11/1974 | Paraskevas | 356/34 |

OTHER PUBLICATIONS

"Brush-on Coatings Can Brighten Up Stress Analysis," from The Engineer, Jun. 8, 1972, pp. 30, 31.
"Observation on Deformation Behaviors in Autobody Panel by Photoelastic Coating Methods," by Abe et al., cited in SAE Paper 760,205, Oct. 1972.

*Primary Examiner*—James J. Gill
*Attorney, Agent, or Firm*—Baldwin & Newtson

[57] ABSTRACT

There is disclosed a method of analyzing formability, strain level, or a related physical characteristic of a given material for a blank which is formed into a desired shape comprising: providing a blank of said given material; applying a flowable photoelastic coating directly on a selected surface area of the blank which is to be analyzed and allowing the coating to cure; forming the blank into the desired shape, and subjecting the coating to analysis. Also disclosed is a novel calibration technique for quantitatively analyzing strain in the plastic region of the metal.

20 Claims, No Drawings

PHOTOELASTIC STAMPING ANALYSIS

BACKGROUND AND SUMMARY OF THE INVENTION

The development of fuel efficient vehicles is a marketable goal for the automotive industry. To help achieve this goal, automotive manufacturers are acting to reduce total vehicle weight. To accomplish vehicle weight reduction, the interacting use of high strength-to-weight ratio materials has been proposed and developed. One vehicle, The Charger XL, by Chrysler Corporation, has achieved a weight savings in excess of 600 pounds (281 kg) by incorporating extensive amounts of high strength steel and aluminum. This approach to weight reduction has proven feasible and could be accommodated in the designs of future automotive products.

In most cases, however, the direct substitution of high strength steel or aluminum into a mild steel part, requires a substantial amount of material development work. New design and manufacturing complexities must be accommodated to meet the required quality and performance objectives, currently met by mild steel parts. Formability, stiffness requirements, dent resistance, draw die overcrown, gage specification, etc., are complexities encountered when selecting new materials for stamped components. To accommodate these new complexities, effective design criteria, and efficient manufacturing evaluation techniques are desirable. A thorough understanding of material performance parameters will insure that costly delays and missed production deadlines are avoided.

Design criteria for dent resistance panel stiffness and draw die overcrown are well established in the literature. However, determining the formability requirements for a stamped sheet metal part, when applying new materials, is a far more elusive problem.

Trying to predict and evaluate the press performance of a new material is a learning curve process. To fabricate a successful sheet metal stamping requires an intimate understanding of the material properties and a substantial amount of stamping experience. Any tool which accelerates this learning curve process is highly desirable.

Previous attempts at using photoelastic analysis, insofar as are known to applicant, have been unsuccessful in evaluating formability of materials. One prior technique involved the casting of a photoelastic coating on a flat teflon sheet and then bonding the cast coating on the blank. As the blank and coating are formed into the desired shape, the coating would begin to delaminate at very low strain levels. Moreover, a special reflective substance had to be incorporated in the bonding adhesive so that a polariscope could even be used to analyze the very low strain levels which were the maximum that could be obtained and which, from a practical standpoint, are generally useless.

The present invention relates to photoelastic stamping analysis, a new technique which assists in resolving manufacturing problems related to stamped metal parts such as automobile body stampings. The invention employs the use of a thin photoelastic coating which is applied in flowable form directly onto a metal blank and allowed to cure. The metal blank with the thin photoelastic coating cast thereon is then formed into a stamped part by any suitable forming means, for example, by means of experimental or production dies. The photoelastic coating is then analyzed to present the complete overall strain distribution in the part. With the photoelastic stamping analysis technique of the present invention, photoelastic strain measurement capabilities are extended from the elastic region to cover the total range of plastic deformation of the part. Also strain levels of up to 35% are reached without the coating delaminating, and a separate reflective coating is not required because the metal itself provides reflectivity. By analyzing the quantity and distribution of plastic deformation in the formed part, an understanding is achieved of three important factors relating to the forming process, these three factors being material, process and shape. The response of the coating can be analyzed both qualitatively and quantitatively as desired. Visual qualitative observations of the isochromatic fringe patterns can provide an intuitive understanding of desirable material forming characteristics. Such qualitative observations are useful for identifying three important types of forming strain activity: (1) areas of no strain activity; (2) areas of high strain gradient; (3) areas of material discontinuity (i.e., yield or fracture location). Furthermore, the strain field can be analyzed at different stages of formation of a part to thereby provide an understanding of the progression of plastic deformation during the forming process. From a quantitative strain standpoint exact strain measurements can also be obtained with the present invention. The photoelastic stamping analysis technique disclosed herein opens up a whole new opportunity for understanding the press performance of modern sheet materials. Visual, qualitative and quantitative interpretations of forming strain and a careful understanding of materials reveals the influence of the material, process and shape on the manufacturing performance of stamped parts. This information in turn can be used to optimize and develop materials for effective use on a timely basis.

The invention is described in detail in the following description of a preferred embodiment according to the best mode presently contemplated in carrying out the invention.

DESCRIPTION OF THE PREFERRED EMBODIMENT

The first step of the method according to the invention is to provide a sheet metal blank of appropriate shape and of a selected material. Next, the surface of the blank is thoroughly cleaned and stripped of its natural contaminants. One way of accomplishing this is by using an acid cleaner and a base solution as a neutralizer. A dam is then built up (for example, using wax strips) around the area of the surface of the blank which is to be coated. It should be mentioned that either selected areas of the blank may be selectively coated or the entire blank may be coated. Flowable photoelastic coating material is then applied to the selected areas, for example, being poured directly inside the dammed area. By suitably supporting the blank, the photoelastic coating material flows to form a smooth surface of even thickness. The thickness of the coating is controlled by controlling the volume of coating material applied to the given area. The coating is allowed to cure for a suitable curing time until it has hardened and is tenaciously bonded to the surface of the blank. With the blank having been thus coated, it is now formed into the desired shape by any suitable forming means, for example, by forming in a die. By way of example, a lubrication system of polyethylene and oil may be applied to both sides of the blank, excluding the areas of photoelastic coating, to facilitate forming. As the blank is formed into the desired shape, the photoelastic coating is formed to the same shape as the metal, being stretched and drawn to the same strain levels as the metal at the plastic-metal interface. In this process the complete strain field of the metal stamping is transferred to the photoelastic coating. Depending upon the amount and area of the coating, it may be desirable to adjust the dies to accommodate the added thickness of the coating although the thickness of the actual coating applied to the blank will depend upon the expected strain levels of interest and shape of deformation; a range of 0.010 inch to 0.080 inch for the coating thickness is typical.

In an actual example the photoelastic stamping analysis technique of the invention was applied to a prototype outer door panel section. The photoelastic coating used was "High Elongation Photoelastic Coating PL-2" available from Photolastic Inc., Malvern, Pennsylvania. The resin and hardener, which are mixed together to form the liquid coating, are customarily heated to a temperature of approximately 49° C prior to being mixed. It has been discovered that superior results can be obtained by also heating the clean metal blank to approximately the same temperature. In other words, the resin, the hardener, and the blank are heated in an oven to about 49° C.; the resin and hardener are then immediately mixed to form the liquid coating; and the coating is then applied to the heated blank (which has been properly leveled) to form a smooth surface of even thickness. The liquid is thereafter allowed to cure, preferably in a room temperature environment of about 22° C., to form a hardened, tenaciously bonded coating directly on the metal surface of the blank. In the example, 24 hours of curing time at room temperature was suitable. It is believed that other photoelastic coatings will produce analogous results, for example, PL1, PL3 and PL8, also by Photolastic, Inc.

In accordance with one aspect of the present invention a unique calibration procedure is employed so that plastic strains in the metal may be evaluated. This unique calibration technique involves the recognition that when metal is deformed beyond the elastic region into the plastic region, the fundamental Hooke's law equations for stress do not apply. The photoelastic equations for strain, however, do apply, but only when the photoelastic coating is calibrated for the plastic range of the parent metal.

According to this calibration technique, a tensile test specimen of the parent metal is coated concurrently with the coating of the metal blank using a portion of the liquid photoelastic coating using the same coating technique described above. A standard ASTM tensile test is run on the tensile specimen utilizing ASTM Standard E8-69 "Standard Methods of Tension Testing of Metallic Materials". The converted true strain extensometer data ($\epsilon_t$) and corresponding photoelastic fringe data $N_o$, $N_n$ are recorded during the tensile test to develop a statistical correlation of tensile test true strain data to photoelastic fringe data. The photoelastic fringe data is obtained using a polariscope. Using this information, a plastic range calibration constant $f_p$ is derived using the following equation:

$$f_p = \frac{\epsilon_t}{AN_o - BN_n}$$

where $A$ and $B$ are systems constants for the particular polariscope and are described in "Instruction Manual for 030 Series Reflection Polariscope" by Photolastic, Inc. Substitution of this constant $f_p$ into the following equations which describe the elastic region strain state yield valid strain measurements throughout the plastic deformation region.

$$\epsilon_1 = Cf_p(AN_o - BN_n)$$

$$\epsilon_2 = Cf_p(AN_o - DN_n)$$

$$\gamma_{max} = Cf_pN_n$$

where
  $C$ = correction factor $N_n$ = normal incidence fringe value $N_o$ = oblique incidence fringe value $D$ = another system constant (see above referenced publication)

The correction factor $C$ in the above equation corrects for the effects of plastic reinforcement, bending strain error, and plain strain error. Values for the correction factor, depending upon the particular metal and loading conditions to which the metal is subjected are documented in the literature, and by way of example shown in FIG. 6 of applicant's paper entitled "Photoelastic Stamping Analysis Adds Vision to Automotive Material Developments", S.A.E. Paper 760205 dated February, 1976.

The strain pattern of the photoelastic coating in the formed metal parts may be analyzed quantitatively and-/or qualitatively using conventional analysis techniques and equipment in conjunction with the use of the present invention. With the calibration technique of the invention, quantitative measurements of strength in the material of the part are obtained by obtaining photoelastic fringe data from the areas of interest and then converting these photoelastic measurements into actual strain data by means of the statistical correlation obtained by use of the tensile specimen. Accordingly, with the present invention reliable accurate quantitative strain data is obtained for not only the elastic region of the metal material but also is extended to cover the entire range of plastic deformation of the metal beyond the elastic region. It will be appreciated that in the description of the disclosure presented herein the use of the term photoelastic analysis is intended to cover analysis of a metal both in its elastic region as well as in its plastic region.

What is claimed is:

1. A method of analyzing formability, strain level, or a related physical characteristic of a given material for a blank which is formed into a desired shape comprising:

providing a blank of said given material;
  applying a flowable photoelastic coating as a single layer directly on a selected surface area of the blank which is to be analyzed and allowing the single layer to fully cure and itself form a tenacious bond directly to the surface of the blank material;
  then forming the coated blank into the desired shape; and
  subjecting the coating to analysis;

wherein the perimeter of said selected surface area is dammed prior to application of the coating thereto so as to contain the flowable coating within the selected surface area.

2. The method claimed in claim 1 wherein the flowable coating is applied to the entire surface area of one side of the blank.

3. The method claimed in claim 1 wherein the perimeter is dammed by means of a wax strip.

4. The method claimed in claim 1 wherein the selected surface area is thoroughly cleaned before the coating is applied.

5. The method claimed in claim 4 wherein cleaning is by means of an acid cleaner followed by a base solution as a neutralizer.

6. The method claimed in claim 1 wherein the coating is allowed to cure to a thickness on the order of 0.010 inch to 0.080 inch.

7. The method claimed in claim 1 including the step of heating the blank prior to application of the coating.

8. The method claimed in claim 7 wherein the blank is heated to a temperature of about 49° C.

9. The method claimed in claim 7 wherein the coating is also heated to approximately the same temperature as the blank prior to application thereof to the blank.

10. The method claimed in claim 9 wherein the coating, after having been applied, is allowed to cure at a temperature of about 22° C.

11. The method claimed in claim 9 wherein the coating is made by mixing a resin and a hardener which have both been heated, prior to mixing, to approximately the same temperature as the blank.

12. The method of quantitatively analyzing strain levels in a given material for a blank which is formed into a desired shape comprising:
providing a blank of said given material with a photoelastic coating on a selected surface area thereof;
providing a tensile specimen of said given material with a like photoelastic coating thereon;
performing a tensile test on said specimen and analyzing the coating thereon by photoelastic analysis to obtain correlation of tensile test true strain data to photoelastic fringe data;
forming the blank into the desired shape;
analyzing by photoelastic analysis the coating on the blank; and
using the above-developed correlation to convert the results of the analysis on the blank coating to quantitative strain data.

13. The method claimed in claim 12 wherein said specimen is coated with photoelastic coating from the same batch as the coating applied to the blank.

14. The method claimed in claim 12 wherein both the specimen and the blank are heated prior to application of the coatings thereto.

15. The method claimed in claim 14 wherein the coatings also are heated prior to their application to the specimen and the blank.

16. The method claimed in claim 12 wherein the coating on the blank is applied thereto in flowable form directly on said selected surface area and then allowed to cure.

17. The method claimed in claim 16 wherein the coating on the specimen is applied thereto in flowable form and allowed to cure.

18. The method claimed in claim 12 wherein the tensile test on the specimen includes the plastic deformation range of the blank material.

19. A method of analyzing formability, strain level, or a related physical characteristic of a given material for a blank which is formed into a desired shape comprising:
providing a blank of said given material;
damming the periphery of a selected surface area of the blank which is to be analyzed;
pouring a flowable photoelastic coating onto said blank within the confines of the dammed selected surface area and allowing the coating to cure and itself form a tenacious bond directly to the surface of the blank material;
then forming the coated blank into the desired shape; and
subjecting the coating to analysis.

20. The method set forth in claim 19 wherein the photoelastic coating is poured as a single layer to have a cured thickness on the order of 0.010 inch to 0.080 inch.

* * * * *